Figure 1:
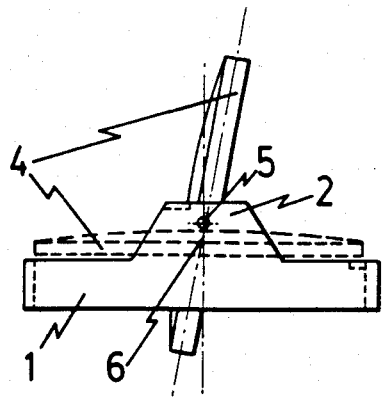

United States Patent [19]

Elosegui

[11] Patent Number: 4,822,354
[45] Date of Patent: Apr. 18, 1989

[54] MECHANICAL VALVULAR PROTHESIS FOR USE IN CARDIAC SURGERY

[76] Inventor: Ignacio M. Elosegui, Ronda de Tejares, 19 - Portal 4 6°, 14008 Cordoba, Spain

[21] Appl. No.: 90,609

[22] Filed: Aug. 28, 1987

[30] Foreign Application Priority Data

Sep. 2, 1986 [ES] Spain .................................. 8600413

[51] Int. Cl.⁴ .............................................. A61F 00/00
[52] U.S. Cl. ...................................................... 623/2
[58] Field of Search .............................. 623/2; 251/65; 137/527.8, 527

[56] References Cited

FOREIGN PATENT DOCUMENTS 0023797 2/1981 European Pat. Off. ................. 623/2
2091386 7/1982 United Kingdom ..................... 623/2
2102101 1/1983 United Kingdom ..................... 623/2

Primary Examiner—Richard J. Apley
Assistant Examiner—David J. Isabella
Attorney, Agent, or Firm—Ladas & Parry

[57] ABSTRACT

The mechanical valvular prothesis for use in cardiac surgery proposed by the invention is constituted by a ring with a concave-convex swinging ring mounted in the contour thereof. The ring is provided with diametrically opposed projections at a same side thereof, the projection has inclined slots thereon. The disc is provided with a pair of appendixes that engage in both inclined slots of the ring, making it capable of translation displacement, in order to determine two approximately equal aperture passages.

An inwardly projecting butt acts as a stop for the disc in the closure position and another two butts near the support points of the rotation axle of the disc, act as stop for the disc in the aperture position.

The disc appendixes bend backwards in order to enhance the displacement thereof and to achieve a balanced aperture of the two halves of the surface limited by the ring itself.

6 Claims, 1 Drawing Sheet

U.S. Patent      Apr. 18, 1989      4,822,354

MECHANICAL VALVULAR PROTHESIS FOR USE IN CARDIAC SURGERY

This invention, as stated in the description, refers to a mechanical valvular prothesis for use in cardiology, which has been designed and developed in order to achieve numerous important advantages over other existing means of analogous aims.

The valvular prothesis object of the invention is of the ring type with a disc located at its contour, which swings to a position where the angle with the ring plane is lesser than 90°. This permits blood flow. When the disc occupies a position in the same plane as the ring, it stops blood flow.

Numerous models of valvular protheses presenting many disadvantages and problems have been designed since the commencement of cardiac valvular surgery. The most important problems are, firstly, the deterioration of hemodynamic gradients, especially in small-bore protheses and, secondly, the incidence of thrombo-embolism caused by the thrombogenicity of the materials used and by differences in flow velocity in different parts of the aperture surface of the ring, as well as different washing levels on the two sides of the disc.

Although durability conditions have been satisfactorily achieved nowadays, it is necessary to achieve designs which take maximum advantage of the valve area, reducing zones of turbulence and slow flow, so that said flow has similar characteristics with respect to a central flow, that is, to achieve that blood flow is almost identical over the entire valvular area.

Thus, prothesic disc valves have the serious problem that they do not open with orifices similar in area and flow velocity, as all of them have at least one orifice of slow flow where thrombosis and disc stiffening problems originate with the subsequent and constant need for anticoagulant therapy.

Taking these factors into account, this invention for a new valvular prothesis for use in cardiology has been specially designed to give two opening orifices or passages, so that both halves of the aperture are similar and permit comparable flow levels.

On the other hand, the valvular prothesis to which we refer has been constructed to permit a simplification in the support system of the disc, in order to reduce gradients (pressure differences between two parts of the flow) and possible thrombosis zones.

Thus, the valvular prothesis according to the invention improves hemodynamic conditions, reducing at the same time the possibilities of thrombo-embolism and reducing, partially at least, the need for anticoagulant medication in the patient.

Basically, the valve of the invention consists, as it was said at the beginning, of a ring and a disc, so that the ring has a coupling means for the disc permitting the oscillation of the latter together with a change in position in a forward sense, all that so that in the aperture position, the final area of the aperture is divided into two approximately equal halves.

The coupling means are provided at lateral and peripheral extensions of the ring, whereat prolongations have been provided which determine butts that limit the angle of aperture to the desired level. Another butt for the closure of the disc is situated at the anterior part, in a position opposite the aforementioned prolongations.

It must be pointed out that the inner and interior faces of the peripheral prolongations constituting the coupling means of the ring have been duly reduced to enable fitting of the area of greatest diameter of the disc during the phases of aperture and closure.

The disc is provided with two pivots which move freely in the coupling means of the peripheral prolongations of the ring.

It has also been foreseen that the part corresponding to the smaller arm of the disc lever, near what would initially be the smaller orifice, would have a concave-convex configuration, so that the face which lies on the opening butts would be convex and forming an angle of 90° with the ring plane, as far as the small arm of the disc is concerned, i.e., the one that closes the part corresponding to the smaller orifice in other disc protheses, whilst the angle which this convexity would form with the horizontal plane of the disc would be equal to 90° minus the angle of aperture of the longer arm of the disc with respect to the ring plane, all values being approximate.

Finally, it must be mentioned that the closure has three supports for the disc; two of them are constituted by the terminal prolongations where the ring sets and the third one is the aforementioned butt on the opposite side, so that thorugh these three supports, traumatic contact of the blood with the rest of the ring is avoided, thus avoiding traumatic impact of the blood with the periphery of the ring and subsequent rupture of blood corpuscles.

A single sheet of diagrams accompanies this description in order to complete it and to facilitate the comprehension of the characteristics of the invention, the figures of which represent the following:

FIG. 1: Side elevational view of the valvular prothesis performed according to the invention.

Figure 2:
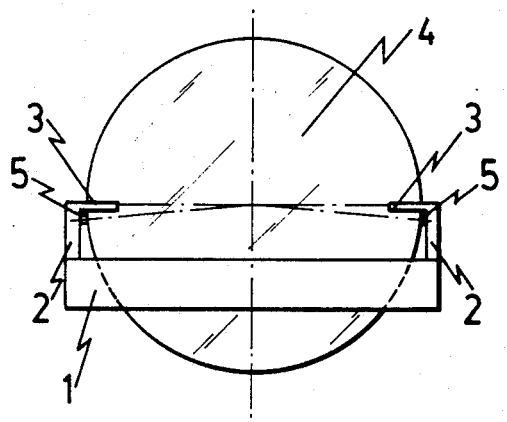

FIG. 2: Plant view of the valvular prothesis with the disc in a vertical plane giving two approximately equal apertures in the ring.

Figure 3:
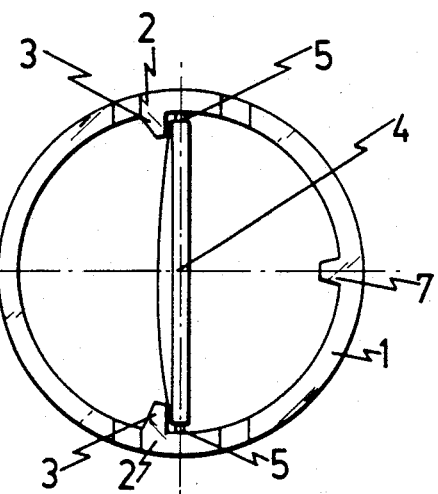

FIG. 3: Diametrical sectional view of the valvular prothesis with the disc in the aperture position, i.e., perpendicular to the ring plane.

Figure 4:
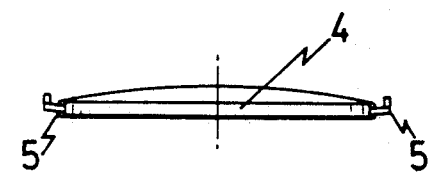
Figure 5:
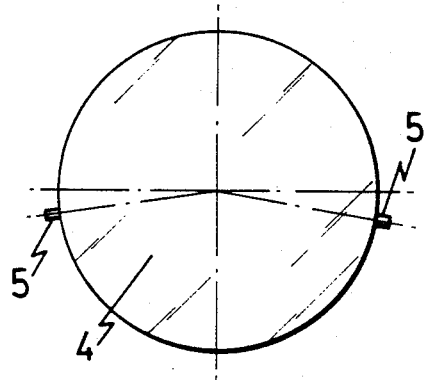

FIGS. 4 and 5: Side and plant views of the disc.

Figure 6:
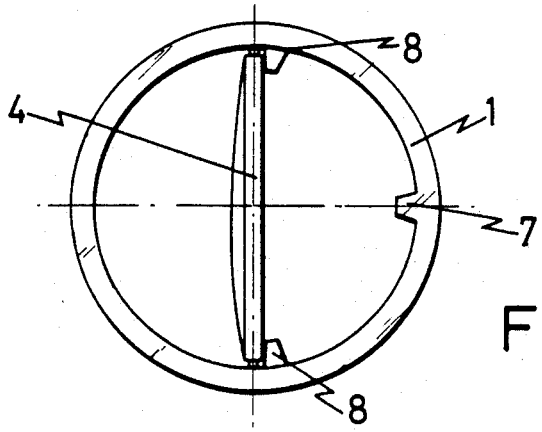

FIG. 6: View similar to FIG. 3 with the aperture butts of the disc below the support plane of the latter.

From the figures which have been commented, it may be observed how the valvular prothesis object of the invention is constituted by a ring 1 with two lateral external prolongations 2 which bend by their end edge to determine the butts 3 which will be described later.

The aforementioned lateral prolongations 2 posses coupling means for a disc 4, which has a pair of appendixes 5 fitting into their corresponding slots in the inner face of the prolongations 2, the slots logically constituting the means of coupling of the aforementioned disc 4.

The appendixes 5 of the disc 4, as the slots for the appendixes 5 are located at areas which are not diametrically opposite, so that when the disc 4 is in a horizontal disposition, it is concentric to ring 1. However, when the disc 4 is placed in a vertical position for aperture, and so that two approximately equivalent passages are formed, it is necessary for the disc 4, besides swinging about its point of articulation, to move in order to occupy an approximately diametric zone with respect to ring 1. In provision for this, the coupling means are prolonged into a slot 6 through which the respective pivot 5 of the disc 4 slides to produce the simultaneous oscillation and displacement of the latter in a forward sense, so that the final area of the aperture is divided into two approximately equal halves, as shown in FIG. 2.

The pivots 5 for coupling with the disc 4 have a special shape, so that backward prolongation produces an additional displacement in a forward sense, and, due to the effect of a double lever mechanism, the potentiation of the aperture lever and thus a greater stability of the disc 4 in the aperture position are produced. The double aperture lever is thus formed by two components: the longer arm of the disc 4 and the posterior prolongation of the pivots 5 of the disc 4.

On the other hand, the sum of the effects produced by the inclination of the slot 6 for coupling with the ring 1 and the posterior prolongation of the pivots 5 of the disc 4 and the concave-convex or angular shape of such a disc 4, produce the effect of balanced aperture of the two halves of the surface limited by the ring 1 and a greater stability of the disc 4 in the aperture position.

The angle of aperture of the disc 4 is limited by the butts 3 previously mentioned, as it may be clearly seen in FIG. 2, while the closure level of the unit is achieved by a butt 7 on the edge of the ring 1 opposite that of the emergence of the prolongations 2 and, as a consequence, that of the butts 3.

That is to say, the closure has three points of support, two of which are constituted by the pivots or appendixes 5 of the disc 4 and the other by the butt 7, thus avoiding traumatic contact of the blood with the rest of the ring. As a consequence of this form of closure of the disc 4 with respect to the ring 1, the disc remains in a plane which is slightly separated from the ring plane 1, thus avoiding the traumatic impact of the blood with the periphery of the ring and the subsequent rupture of the blood corpuscles, and, at the same time, facilitating the cleansing of the disc 4 and the ring 1.

The butts limiting the aperture of the disc and which are marked with 3 in FIGS. 2 and 3, may also be located such as shown in FIG. 6 with 8, working both as aperture and as closure butts, thus reinforcing the effect of the butt 7 of FIG. 3 and reducing the stress in pivots 5 of FIG. 4. Butts 8 are located in an emerging position with respect to the ring 1, such as butts 3 were and they are coplanar with butt 7.

Finally, it should be pointed out that the metallic ring of the prothesis is included in a conventional ring for biological suture of the prothesis of the own rings of the patient's heart. The metallic ring must be able to rotate (roll or circulate) within the suture ring, similarly to conventional protheses.

I claim:

1. A mechanical valvular prothesis comprising:
a ring having an interior surface, an exterior surface, an upper downstream rim surface, a lower upstream rim surface, and an upper and lower opening formed by the interior surface;
at least one butt, essentially flush with the upper downstream rim surface, inwardly extending from the interior surface of the ring;
at least two flanges upwardly extending from the upper downstream rim, said flanges having at least one inclined slot thereon;
at least one tab inwardly extending from an upper portion of the flanges; and
a disc, having a top side, a bottom side, a peripheral rim, and at least two pivots extending from the disc in a nondiametrical manner, said disc is positioned between the flanges so that the pivots can extend into the slots and permit the disc to have both translational and rotational movement, wherein the disc moves from a closed first position, in which the disc covers the upper opening and rests on the butt so that the bottom side of said disc is slightly spaced above and parallel to the upper rim surface, to an open second position in which the disc rests against the tabs so as to form approximately equal passages on either side of the disc.

2. A valvular prothesis according to claim 1, wherein the top side of the disc has a convex shape and the bottom side has a concave shape, and wherein the disc in the open position has an anterior region downstream of the pivots and a smaller posterior region upstream of the pivots so that the disc will have greater stability in the open position.

3. A mechanical valvular prothesis comprising:
a ring having an interior surface, an exterior surface, an upper downstream rim surface, a lower upstream rim surface, and an upper and lower opening formed by the interior surface;
at least one butt, essentially flush with the upper downstream rim surface, inwardly extending from the interior surface of the ring;
at least two flanges upwardly extending from the upper downstream rim, said flanges having at least one inclined slot thereon;
at least one shoulder, essentially flush with the upper downstream rim surface, inwardly extending from the interior surface of the ring; and
a disc, having a top side, a bottom side, a peripheral rim, and at least two pivots extending from the disc in a nondiametrical manner, said disc is positioned between the flanges so that the pivots can extend into the slots and permit the disc to have both translational and rotational movement, wherein the disc moves from a closed first position, in which the disc covers the upper opening and rests on the butt and shoulder so that the bottom side of said disc is slightly spaced above and parallel to the upper rim surface, to an open second position in which the disc rests against the shoulder so as to form approximately equal passages on either side of the disc.

4. A valvular prothesis according to claim 3, wherein the top side at the disc has a convex shape and the bottom side has a concave shape, and wherein the disc in the open position has an anterior region downstream of the pivots and a smaller posterior region upstream of the pivots so that the disc will have greater stability in the open position.

5. A mechanical valvular prothesis comprising:
a ring having an interior surface, an exterior surface, an upper downstream rim surface, a lower upstream rim surface, and an upper and lower opening formed by the interior surface;
at least one butt, essentially flush with the upper downstream rim surface, inwardly extending from the interior surface of the ring;
at least two flanges upwardly extending from the upper downstream rim, said flanges having at least one inclined slot thereon;
at least one shoulder, essentially flush with the upper downstream rim surface, inwardly extending from the interior surface of the ring;
at least one tab inwardly extending from an upper portion of the flanges; and
a disc, having a top side, a bottom side, a peripheral rim, and at least two pivots extending from the disc in a nondiametrical manner, said disc is positioned between the flanges so that the pivots can extend into the slots and permit the disc to have both translational and rotational movement, wherein the disc moves from a closed first position, in which the disc covers the upper opening and rests on the butt and shoulder so that the bottom side of said disc is slightly spaced above and parallel to the upper rim surface, to an open second position in which the disc rests against the tab and shoulder so as to form approximately equal passages on either side of the disc.

6. A valvular prothesis according to claim 5, wherein the top side at the disc has a convex shape and the bottom side has a concave shape, and wherein the disc in the open position has an anterior region downstream of the pivots and a smaller posterior region upstream of the pivots so that the disc will have greater stability in the open position.

* * * * *